(12) United States Patent
Kim et al.

(10) Patent No.: US 11,040,153 B2
(45) Date of Patent: Jun. 22, 2021

(54) SYRINGE ADAPTER WITH SECURE CONNECTION

(71) Applicant: Becton Dickinson and Company Limited, Dun Laoghaire (IE)

(72) Inventors: Jayeon Kim, River Edge, NJ (US); Christopher Lee, Union City, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 132 days.

(21) Appl. No.: 16/381,489

(22) Filed: Apr. 11, 2019

(65) Prior Publication Data

US 2019/0321564 A1 Oct. 24, 2019

Related U.S. Application Data

(60) Provisional application No. 62/659,854, filed on Apr. 19, 2018.

(51) Int. Cl.
A61M 5/34 (2006.01)

(52) U.S. Cl.
CPC ............ *A61M 5/345* (2013.01); *A61M 5/347* (2013.01); *A61M 5/348* (2013.01)

(58) Field of Classification Search
CPC ...... A61M 5/345; A61M 5/348; A61M 5/347; A61M 2039/1016; A61M 2039/1033; A61M 2039/1044; A61M 2039/1077; A61M 39/1011; A61M 39/10; A61M 2039/1005; A61M 39/1055; A61M 2039/1066; A61M 5/346; A61M 5/344; A61M 2039/1093; A61M 2039/1088
See application file for complete search history.

(56) References Cited

U.S. PATENT DOCUMENTS

| 4,573,978 | A | 3/1986 | Reilly |
| 5,620,427 | A | 4/1997 | Werschmidt et al. |
| 8,777,931 | B2 | 7/2014 | Davis et al. |
| 2013/0006211 | A1 | 1/2013 | Takemoto |
| 2015/0297453 | A1* | 10/2015 | Kim .................... A61J 1/2055 285/92 |
| 2016/0136412 | A1* | 5/2016 | McKinnon ......... A61M 39/1011 604/256 |
| 2016/0250415 | A1* | 9/2016 | Yagi .................. A61M 39/1011 604/187 |

* cited by examiner

*Primary Examiner* — Bhisma Mehta
*Assistant Examiner* — Robert F Allen
(74) *Attorney, Agent, or Firm* — The Webb Law Firm

(57) ABSTRACT

A syringe adapter includes a housing having a first end and a second end positioned opposite the first end, with the housing defining a passageway, and a connector body having a first end and a second end positioned opposite the first end, with the connector body having a connection member configured to be secured to a mating connector. One of the housing and the connector body includes a tab and the other of the housing and the connector body defines a channel that receives the tab, with the connector body movable relative to the housing between a first position where the connector body is restricted from rotating relative to the housing in a first rotational direction and free to rotate relative to the housing in a second rotational direction, and a second position where the connector body is free to rotate in the first and second rotational directions.

19 Claims, 11 Drawing Sheets

SYRINGE ADAPTER WITH SECURE CONNECTION

CROSS-REFERENCE TO RELATED APPLICATION

The present application claims priority to U.S. Provisional Application Ser. No. 62/659,854, entitled "Syringe Adapter with Secure Connection", filed Apr. 19, 2018, the entire disclosure of which is hereby incorporated by reference in its entirety.

BACKGROUND OF THE INVENTION

Field of the Invention

The present invention relates to a syringe adapter and, more particularly, to a syringe adapter having a secure connection feature.

Description of Related Art

Healthcare workers, such as pharmacists and nurses, can be subject to acute and long term health risks upon repeated exposure to drugs or solvents which might escape into the air during drug preparation, drug administration, and other similar handling. This problem is particularly serious when cytotoxins, antiviral drugs, antibiotics, and radiopharmaceuticals are concerned. The health risks faced by exposure to these drugs can include the development of cancer, reproductive problems, genetic conditions, and other serious concerns. Other hazardous areas may be sample taking, such as samples concerning virus infections or the like. When performing infusions, it is often necessary to inject a drug or other medical substance into the infusion fluid, inside an infusion bag or other infusion fluid container. This is often done by means of penetrating a septum or other fluid barrier of an injection port on the infusion bag or on the infusion fluid line with a needle of a syringe filled with the medical fluid in question. However, even before this, it may be necessary to transfer the medical fluid from a vial to a syringe and then from the syringe to a secondary container. In each of these steps, staff may be exposed to the medical fluid by means of contamination. Such contamination may be vaporized medical fluid or aerosol in the air. The contaminations may contaminate the staff through their lungs, or by vaporized medical fluid or aerosol in the air which condensates on the skin to thereafter penetrate the skin of the staff. Some medicaments are even known to penetrate protection gloves and, thereby, contaminate the staff.

Exposure to contaminations like this may, on a long term basis, give rise to high concentrations of medicaments in the blood or the human body of the staff as described above. It has been understood that, due to the many transferring steps between containers e.g., vials, syringes, infusion systems, etc., the risk for contamination during the actual insertion and retraction of a needle from the container, e.g., a vial, needs to be contained. Closed system transfer devices (CSTDs) have been developed to ensure that the medicament is contained in the transfer device during transfer of the medicament.

Generally, a CSTD includes a syringe adapter for connection to a syringe and an adapter for connection to a vial, a second syringe, or a conduit providing fluid access to the patient's circulatory system. According to one arrangement, the healthcare practitioner may reconstitute a powdered or lyophilized compound with saline or some other reconstitution medium by attaching the syringe to the vial via connection of the respective adapters, reconstituting the drug, aspirating the compound into the syringe, disconnecting the adapters, and then attaching the syringe to the fluid conduit through the respective adapters to a patient delivery device, such as an IV line or syringe for administration to the patient.

One type of an adapter that can be used in a CSTD has a first connector having a male or female luer-lock element that is arranged to be joined with a corresponding female or male luer-lock element of a second connector component. According to one aspect, the second connector component can be a patient delivery device, such as an IV line or a syringe. The luer-lock element can, thus, be screwed into and unscrewed from the corresponding luer-lock element. It is desirable to prevent an accidental or inadvertent unscrewing of the components, which could lead to the disconnection of the fluid passage. Such disconnection may entail a serious contamination risk for a patient and/or any other person in the vicinity of the disconnected medical connector. The issue of safety in administration of hazardous medical compounds is one that has been identified as being of critical importance by professional organizations and government agencies alike.

It is, therefore, desirable to provide an adapter for enabling fluid transfer between the first connector and the second connector by facilitating a positive connection of the connectors and avoiding inadvertent or accidental disconnection of the connectors.

SUMMARY OF THE INVENTION

According to one aspect, a medical connector includes a housing having a first end and a second end positioned opposite the first end, with the housing defining a passageway, and a connector body having a first end and a second end positioned opposite the first end, with the connector body having a connection member configured to be secured to a mating connector. One of the housing and the connector body includes a tab and the other of the housing and the connector body defines a channel that receives the tab, with the connector body movable relative to the housing between a first position where the connector body is restricted from rotating relative to the housing in a first rotational direction and free to rotate relative to the housing in a second rotational direction, and a second position where the connector body is free to rotate in the first and second rotational directions.

The channel may include a start portion, a connecting portion extending from the start portion, and a connected portion extending from the connecting portion, where the connector body is in the first position when the tab is in the start portion of the channel, the connector body is in the second position when the tab is in the connected portion of the channel, and where the tab is in the connecting portion of the channel when the connector body transitions from the first position to the second position. The medical connector may further include a stop face adjacent to the start portion of the channel, with the stop face configured to engage the tab of the housing to restrict movement of the housing in the first rotational direction. The connected portion of the channel may extend circumferentially around the connector body. The connecting portion of the channel may extend helically from the start portion of the channel to the connected portion of the channel, with the connector body configured to axially move relative to the housing when the tab engages the connector body or the housing defining the connecting portion of the channel. The first end of the connector body may be spaced from the first end of the housing when the connector body is in the first position, and the first end of the connector body may be coterminous with the first end of the housing when the connector body is in the second position.

The connection member of the connector body may extend from the first end of the connector body. The connector body may include an indicator visible when the connector body is in the first position and non-visible when the connector body is in the second position.

A depth of the connecting portion of the channel may decrease as the connecting portion extends from the start portion of the channel to the connected portion of the channel.

The channel may include a reset portion extending from the connected portion of the channel to the start portion of the channel, with a depth of the reset portion of the channel decreasing from the connected portion of the channel to the start portion of the channel, where the tab is configured to move from the connected portion of the channel to the start portion of the channel via the reset portion of the channel. The reset portion of the channel may extend in an axial direction.

The tab may be movable in a radial direction via a spring member. The tab may provide at least one of an audible and tactile indication when moved from the first position to the second position. The audible or tactile indication may be the tab engaging the connector body when the connector body is moved into the second position. The spring member may be a cantilever spring.

The connector body may be received by the passageway of the housing, with the tab extending radially inward from the housing into the channel of the connector body. The connection member may be a female luer connection.

In a further aspect, a syringe adapter includes a housing having a first end and a second end positioned opposite the first end, with the housing defining a passageway. The syringe adapter further includes a connector body having a first end and a second end positioned opposite the first end, with the connector body having a connection member configured to be secured to a syringe barrel. One of the housing and the connector body includes a tab and the other of the housing and the connector body includes a channel that receives the tab, with the tab movable in a radial direction via a spring member. The connector body is movable relative to the housing between a first position where the connector body is restricted from rotating relative to the housing in a first rotational direction and free to rotate relative to the housing in a second rotational direction, and a second position where the connector body is free to rotate in the first and second rotational directions. The channel includes a start portion, a connecting portion extending from the start portion, a connected portion extending from the connecting portion, and a reset portion extending from the connected portion of the channel to the start portion of the channel. The connector body is in the first position when the tab is in the start portion of the channel, the connector body is in the second position when the tab is in the connected portion of the channel, and the tab is in the connecting portion of the channel when the connector body transitions from the first position to the second position. The tab is configured to move from the connected portion of the channel to the start portion of the channel via the reset portion of the channel.

The connecting portion of the channel may extend helically from the start portion of the channel to the connected portion of the channel, with the connector body configured to axially move relative to the housing when the tab engages the connector body or housing defining the connecting portion of the channel, where a depth of the rest portion of the channel decreases from the connected portion of the channel to the start portion of the channel, and where a depth of the connecting portion of the channel decreases as the connecting portion extends from the start portion of the channel to the connected portion of the channel. The first end of the connector body may be spaced from the first end of the housing when the connector body is in the first position, and the first end of the connector body may be coterminous with the first end of the housing when the connector body is in the second position.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

Figure 1:
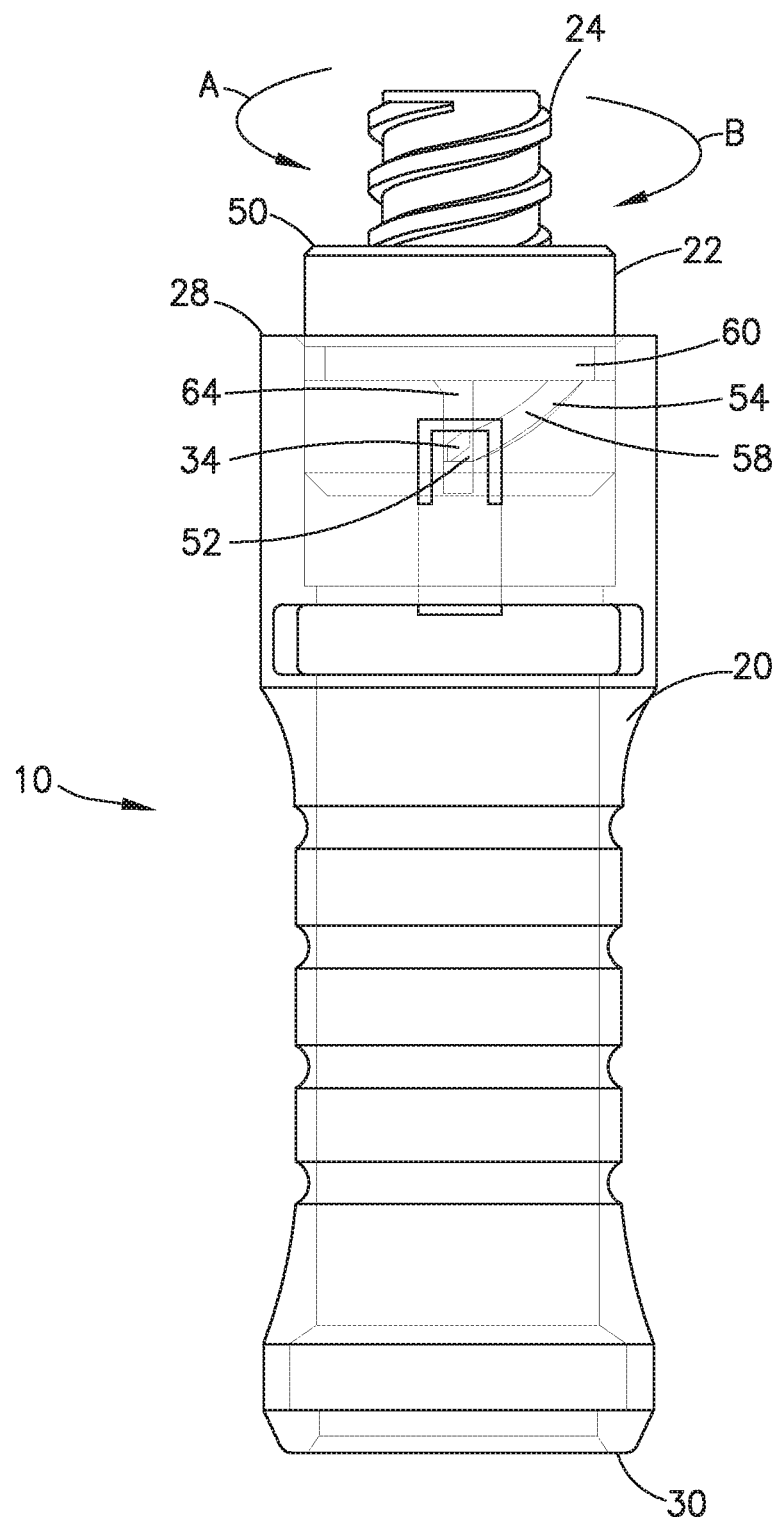
FIG. 1 is front view of a syringe adapter according to one aspect of the present invention, with a housing shown transparent for clarity.

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

Referring to FIGS. 1-11, a syringe adapter 10 according to one aspect of the present invention includes a housing 20 and a connector body 22. The connector body 22 has a connection member 24 configured to be secured to a mating connector. In one aspect, the connection member 24 is a female luer lock connector configured to be secured to a corresponding male luer of a barrel of a syringe. The syringe adapter 10 may be utilized in connection with a closed system transfer device system, which facilitates the closed transfer of fluids between various containers. In particular, the syringe adapter 10 may facilitate the reconstitution of a medicament within a vial, the withdrawal of medicament from the vial, the delivery of medicament to a patient line via a patient connector or to an infusion container via an infusion spike connector, and other related functions with various components of system for the closed transfer of fluids. Although not shown, the syringe adapter 10 may include a cannula, seal arrangement to facilitate the closed transfer of fluids using the cannula, and another connection arrangement to connect to the various components of the system for the closed transfer of fluids. Although the connector body 22 is shown in connection with a syringe adapter 10, the housing 20, and connector body 22 arrangement may be provided on any other suitable medical connector to achieve the advantages discussed in more detail below.

Referring to FIGS. 1-3, 6, and 7, the housing 20 has a first end 28 and a second end 30 positioned opposite the first end 28. The housing 20 defines a passageway 32 and includes a tab 34 extending from the housing 20. The tab 34 extends radially inward from the housing 20 into the passageway 32. The tab 34 is movable in a radial direction via a spring member 36. The spring member 36 may be a cantilever spring formed integrally with the housing 20, although other suitable spring arrangements may be utilized. The tab 34 is generally rectangular, although other suitable shapes and configurations may be utilized. The tab 34 includes an inclined face 38, which is angled relative to a plane that is perpendicular to a longitudinal axis of the housing 20. The passageway 32 extends from the first end 28 to the second end 30 of the housing 20.

Referring to FIGS. 1-5, the connector body 22 has a first end 50 and a second end 52 positioned opposite the first end 50. The connector body 22 defines a channel 54 that receives the tab 34 of the housing 20. The connector body 22 is movable relative to the housing 20 between a first position where the connector body 22 is restricted from rotating relative to the housing 20 in a first rotational direction A and free to rotate relative to the housing 20 in a second rotational direction B, and a second position where the connector body 22 is free to rotate in the first and second rotational directions A,B. The channel 54 includes a start portion 56, a connecting portion 58 extending from the start portion 56, and a connected portion 60 extending from the connecting portion 58. The connector body 22 is in the first position when the tab 34 is in the start portion of the channel 54, the connector body 22 is in the second position when the tab 34 is in the connected portion 60 of the channel 54, and the tab 34 of the housing 20 is in the connecting portion 58 of the channel 54 when the connector body 22 transitions from the first position to the second position. The connector body 22 includes a stop face 62 adjacent to the start portion 56 of the channel 54, with the stop face 62 configured to engage the tab 34 of the housing 20 to restrict movement of the housing 20 in the second rotational direction B. The connected portion 60 of the channel 54 extends circumferentially around the connector body 22, which, as discussed in more detail below, allows the connector body 22 to freely rotate in the first and second rotational directions A,B when the connector body 22 is in the second position.

Figure 4:
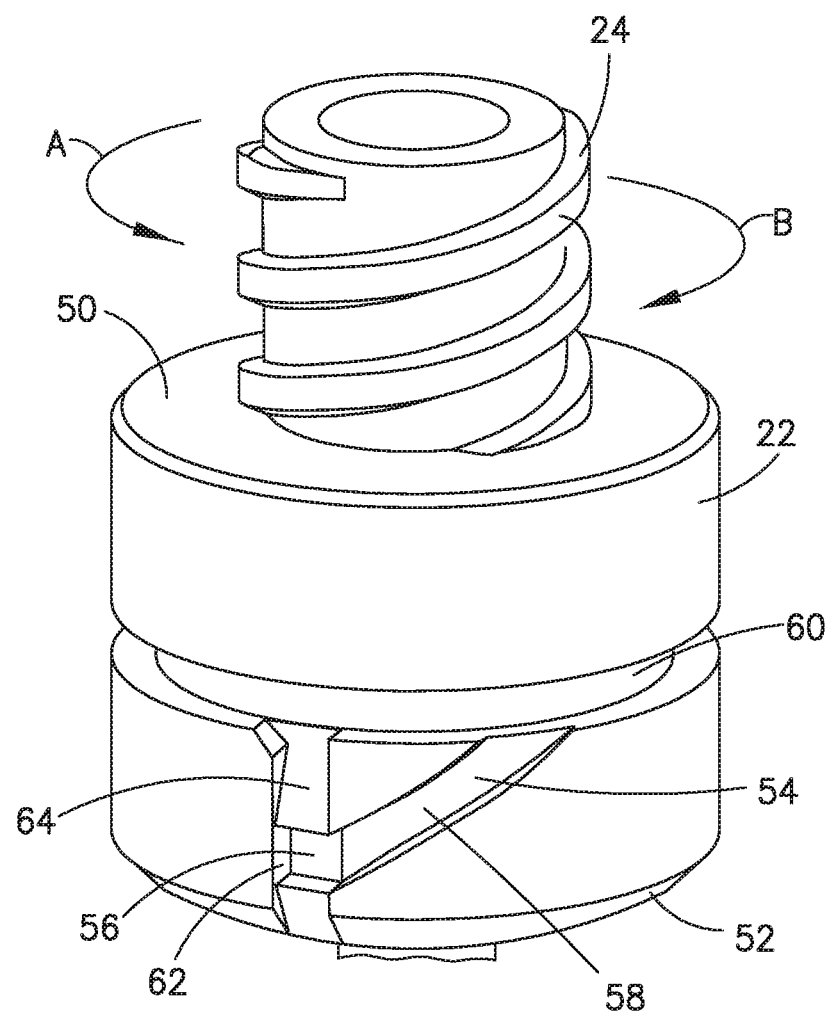
FIG. 4 is a perspective view of a connector body of the syringe adapter of FIG. 1.
Figure 5:
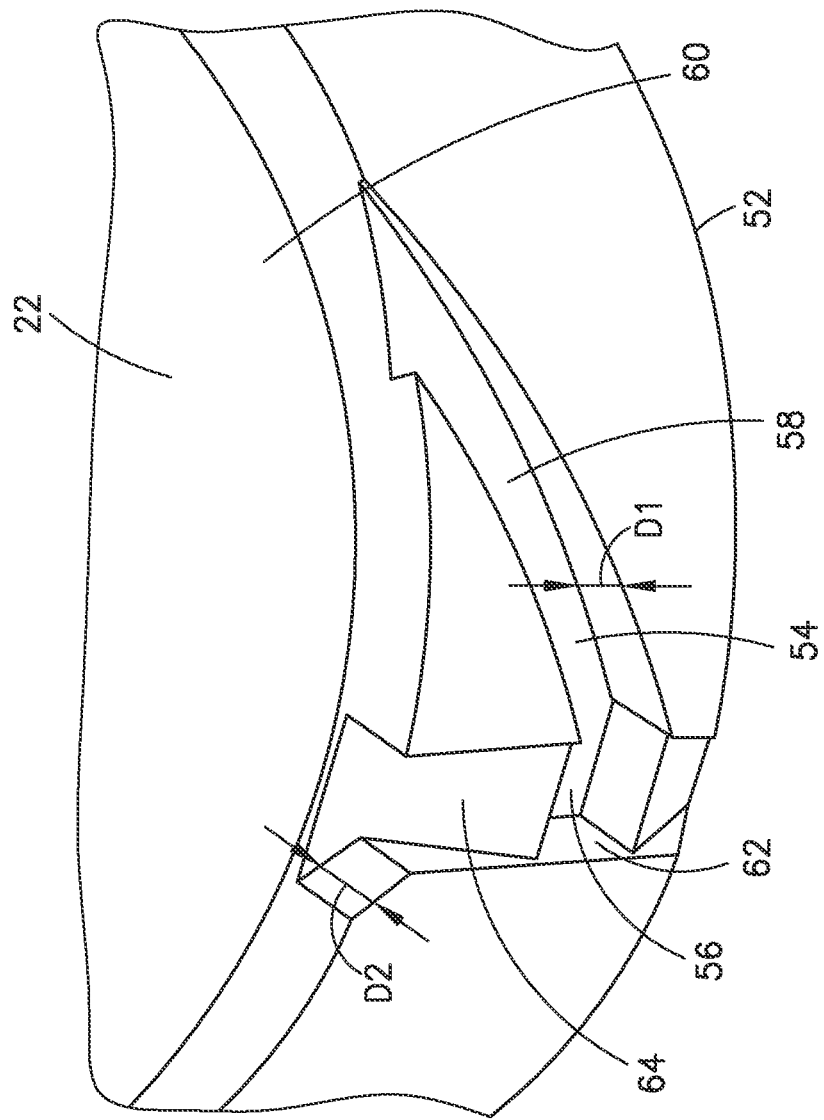
FIG. 5 is an enlarged perspective view of the connector body of FIG. 4.
Figure 6:
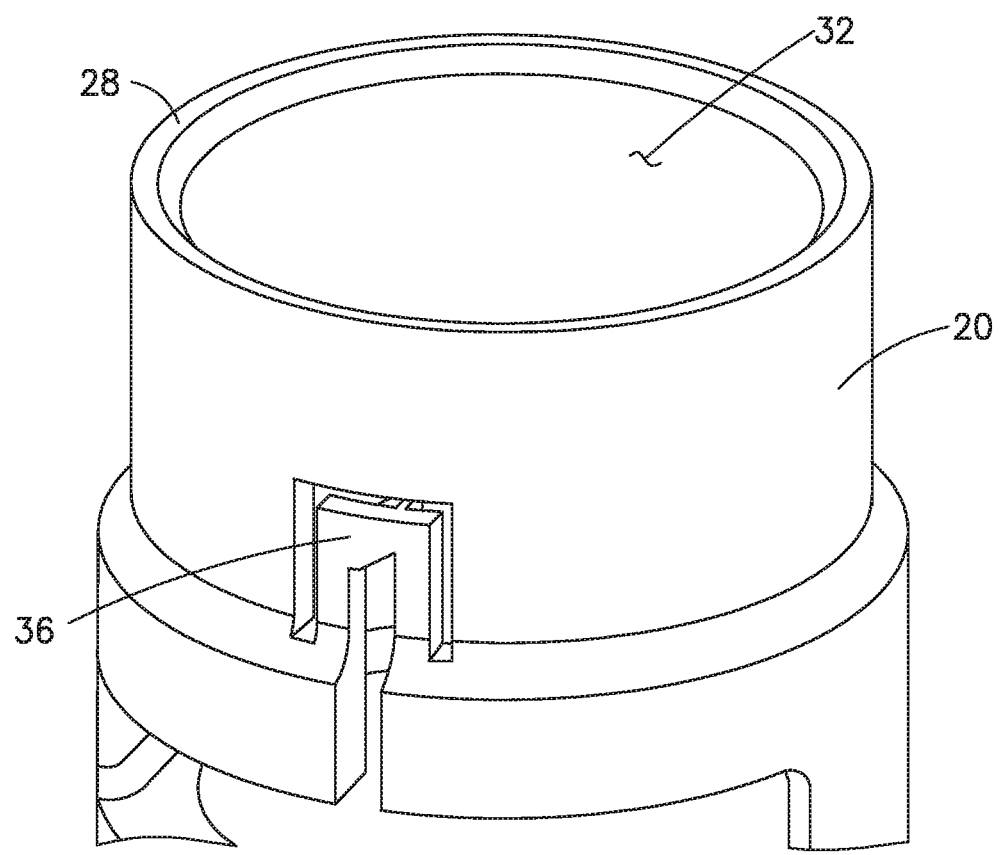
FIG. 6 is a front perspective view of a housing of the syringe adapter of FIG. 1.
Figure 7:
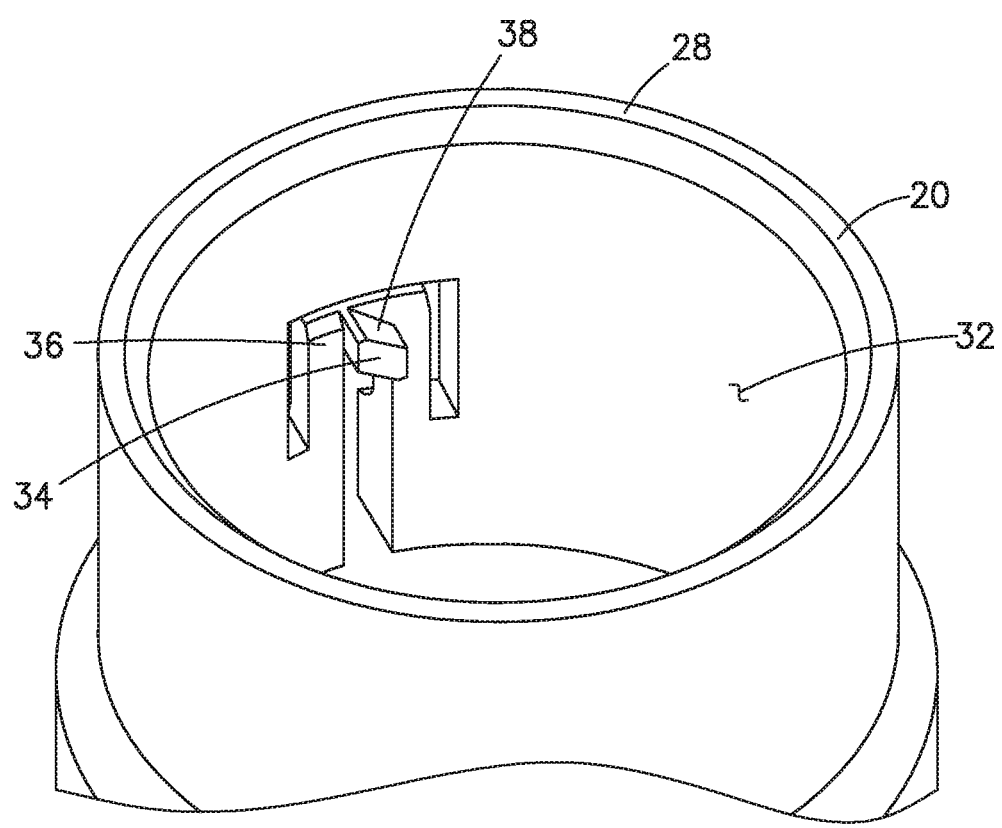
FIG. 7 is a rear perspective view of the housing of FIG. 6.
Figure 8:
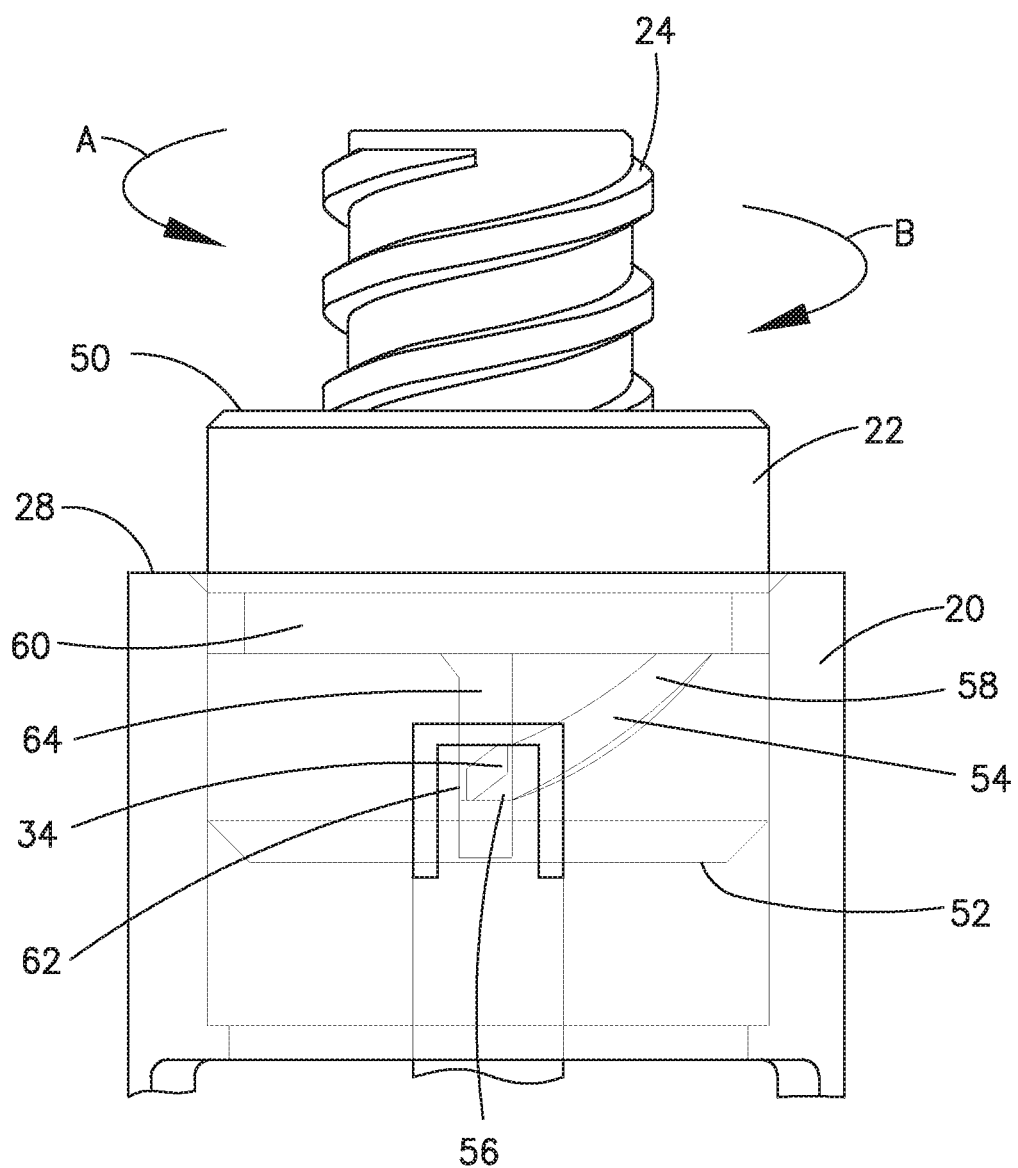
FIG. 8 is a partial front view of the syringe adapter of FIG. 1, showing a first position of a connector body with a housing shown transparent for clarity.

Referring to FIGS. 4 and 5, the connecting portion 58 of the channel 54 extends helically from the start portion 56 of the channel 54 to the connected portion 60 of the channel 54, with the connector body 22 configured to axially move relative to the housing 20 when the tab 34 of the housing 20 engages the connector body 22 within the connecting portion 58 of the channel 54. The first end 50 of the connector body 22 is spaced from the first end 28 of the housing 20 when the connector body 22 is in the first position, and the first end 50 of the connector body 22 is coterminous with the first end 28 of the housing 20 when the connector body 22 is in the second position. The connection member 24 of the connector body 22 extends from the first end 50 of the connector body 22. The connector body 22 may include an indicator visible when the connector body 22 is in the first position and non-visible when the connector body 22 is in the second position. The indicator may be a colored portion of the connector body 22 or indicia on a portion of the connector body 22 that is visible in the first position and non-visible in the second position. A depth D1 of the connecting portion 58 of the channel 54 decreases as the connecting portion 58 extends from the start portion 56 of the channel 54 to the connected portion 60 of the channel 54. The depth D1 of the connecting portion 58 of the channel 54 may gradually decrease as the connecting portion 58 extends toward the connected portion 60 of the channel 54. As discussed in more detail below, the decreasing depth D1 increases the friction and engagement of the connector body 22 with the tab 34 of the housing 20 thereby increasing the torque required to rotate the connector body 22 relative to the housing 20 as the tab 34 moves closer to the connected portion 60 of the channel 54.

Referring again to FIGS. 4 and 5, the channel 54 further includes a reset portion 64 extending from the connected portion 60 of the channel 54 to the start portion 56 of the channel 54. A depth D2 of the reset portion 64 of the channel 54 decreases from the connected portion 60 of the channel 54 to the start portion 56 of the channel 54. The tab 34 of the housing 20 is configured to move from the connected portion 60 of the channel 54 to the start portion 56 of the channel 54 via the reset portion 64 of the channel 54. The decreasing depth D2 of the reset portion 64 of the channel 54, as noted above, prevents the tab 34 from moving to the connected portion 60 of the channel 54 from the start portion 56 of the channel 54 via the reset channel 64. In other words, the shape and configuration of the reset channel 64 prevents the tab 34 from entering the reset portion 64 from the start portion 56. The reset portion 64 of the channel 54 extends in an axial direction of the connector body 22.

The tab 34 provides an audible and/or tactile indication when moved from the first position to the second position. The audible and/or tactile indication may be provided by the tab 34 engaging the connector body 22 when the connector body 22 is moved into the second position. In particular, as the tab 34 moves through the connecting portion 58 of the channel 54, the decreasing depth of the connecting portion 58 biases the tab 34 radially outward via the spring member 36, which not only increases the resistance between the connector body 22 and the housing 20 due to the increased frictional force, but also allows the tab 34 to snap back to its original position when the tab 34 enters the connected portion 60 of the channel 54. Snapping back to its original position causes the tab 34 to engage the connector body 22 and cause an audible and/or tactile indication that the tab 34 has entered the connected portion 60 and that the connector body 22 has moved to the second position.

Figure 2:
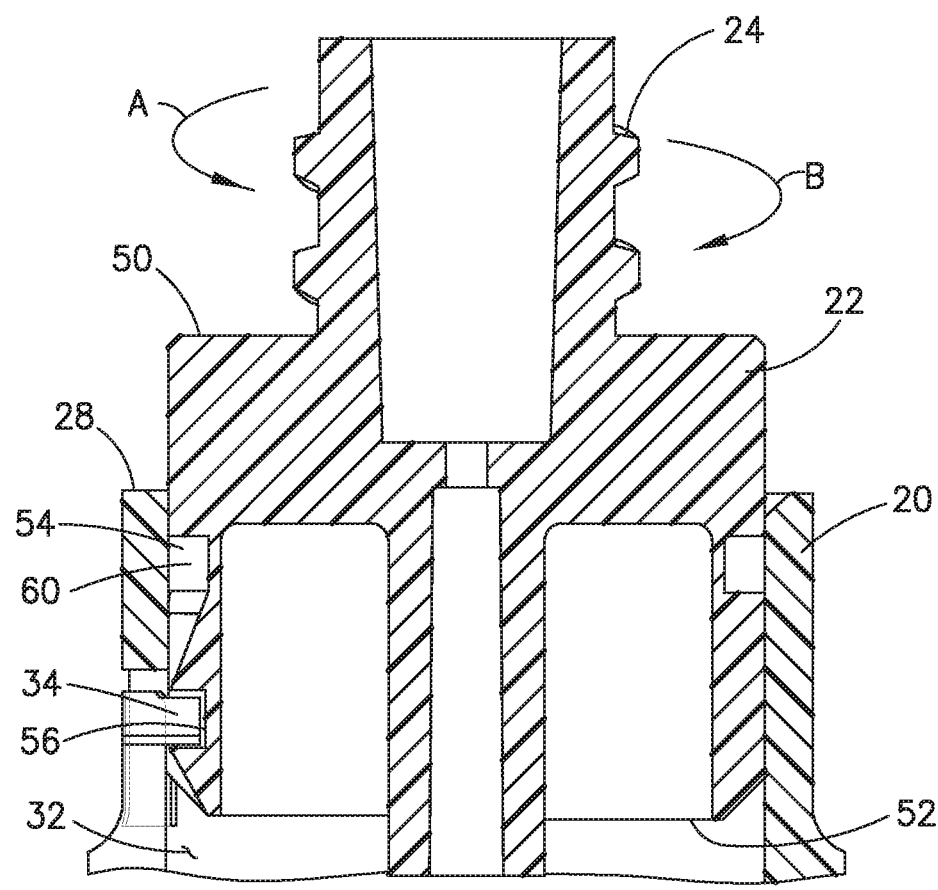
FIG. 2 is a partial cross-sectional view of the syringe adapter of FIG. 1, showing a first position of a connector body.
Figure 3:
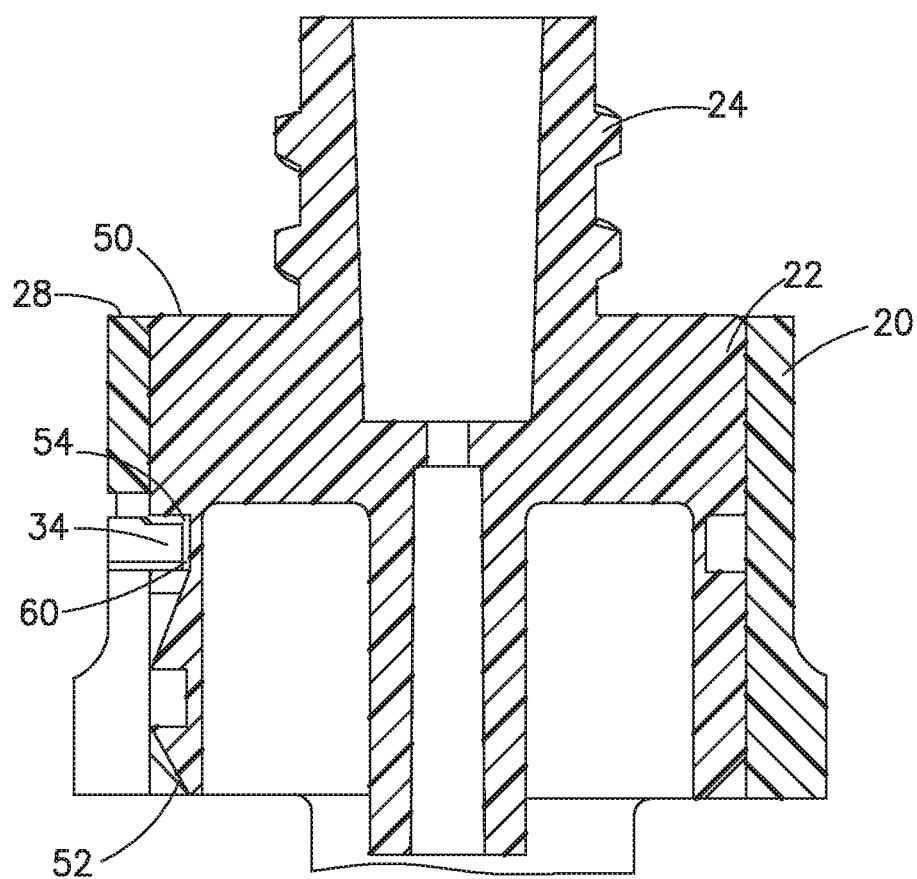
FIG. 3 is a partial cross-sectional view of the syringe adapter of FIG. 1, showing a second position of a connector body.

Referring to FIGS. 1-3, the connector body 22 is received by the passageway 32 of the housing 20, with the tab 34 extending radially inward from the housing 20 into the channel 54 of the connector body 22. The connector body 22, however, may receive the housing 20 with the tab 34 of the housing 20 extending radially outward. Further, although the tab 34 is shown on the housing 20 and the channel 54 provided on the connector body 22, the tab 34 may also be provided on the connector body 22 with the channel 54 being provided on the housing 20.

Figure 9:
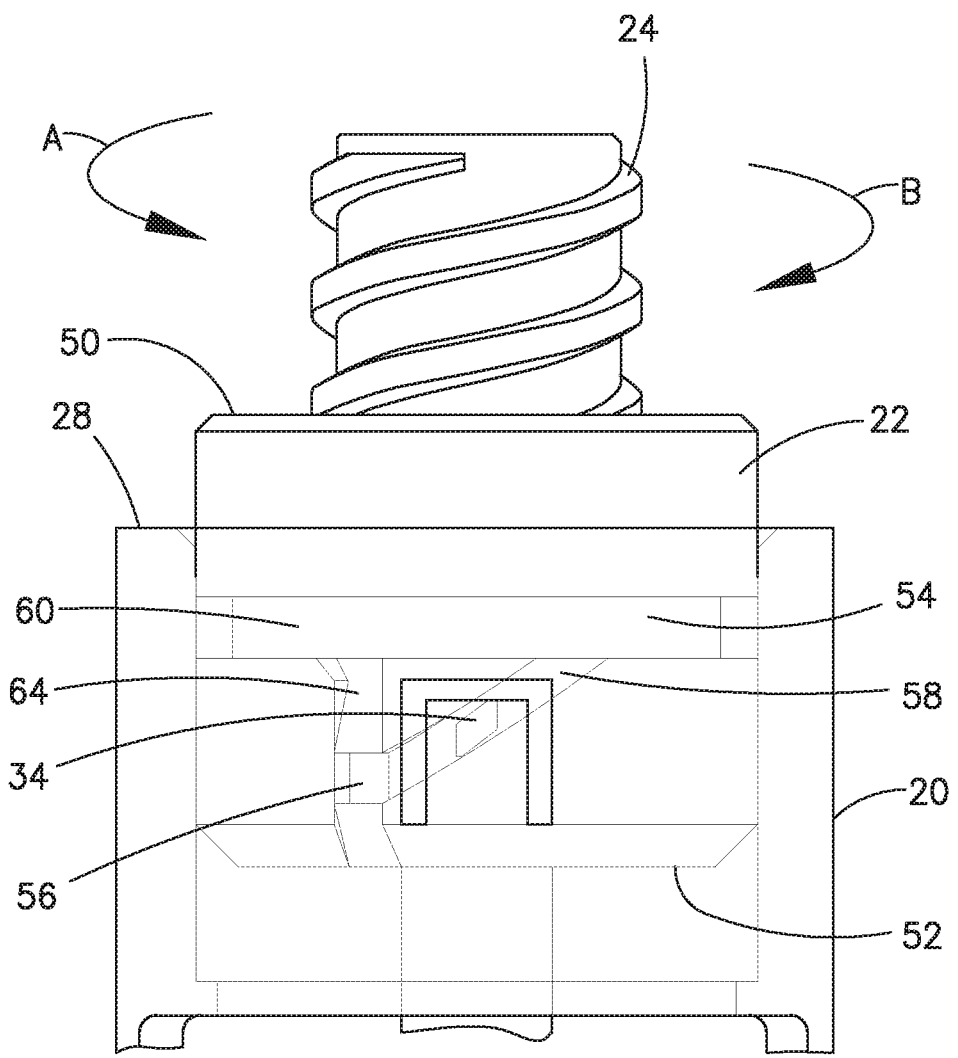
FIG. 9 is a partial front view of the syringe adapter of FIG. 1, showing a connector body transitioning between a first position and a second position with a housing shown transparent for clarity.

Referring to FIGS. 8-11, the use of the syringe adapter 10 and the various positions of the connector body 22 is shown. When the connector body 22 is in the first position (shown in FIG. 8), the first end 50 of the connector body 22 is spaced from the first end 28 of the housing 20 to provide an indication that the connector body 22 is in the first position. In the first position, the tab 34 is in the start portion 56 of the channel 54. To connect a syringe to the connection member 24 of the connector body 22, a male luer lock or other suitable connector is engaged with the connection member 24 and rotated to thread the male luer onto the female luer lock or connection member 24. Once the male luer lock is engaged with the connection member 24 and frictional forces therebetween are increased, further rotation of the male luer lock causes the connector body 22 to rotate in the second rotational direction B relative to the housing 20, which causes the tab 34 to enter the connecting portion 58 of the channel 54, as shown in FIG. 9. When the connector body 22 is in the first position, the stop face 62 prevents the connector body 22 from rotating relative to the housing 20 in the second rotational direction B. As discussed in more detail below, the stop face 62 allows the syringe to be disconnected from the connector body 22 by prevent rotation between connector body 22 and the housing 20.

Referring to FIG. 9, with the tab 34 of the housing 20 within the connecting portion 58 of the channel 54, the engagement between the tab 34 and the connector body 22 and the helical shape of the connecting portion 58 causes axial movement of the connector body 22 relative to the housing 20 in addition to the rotational movement discussed above.

Figure 10:
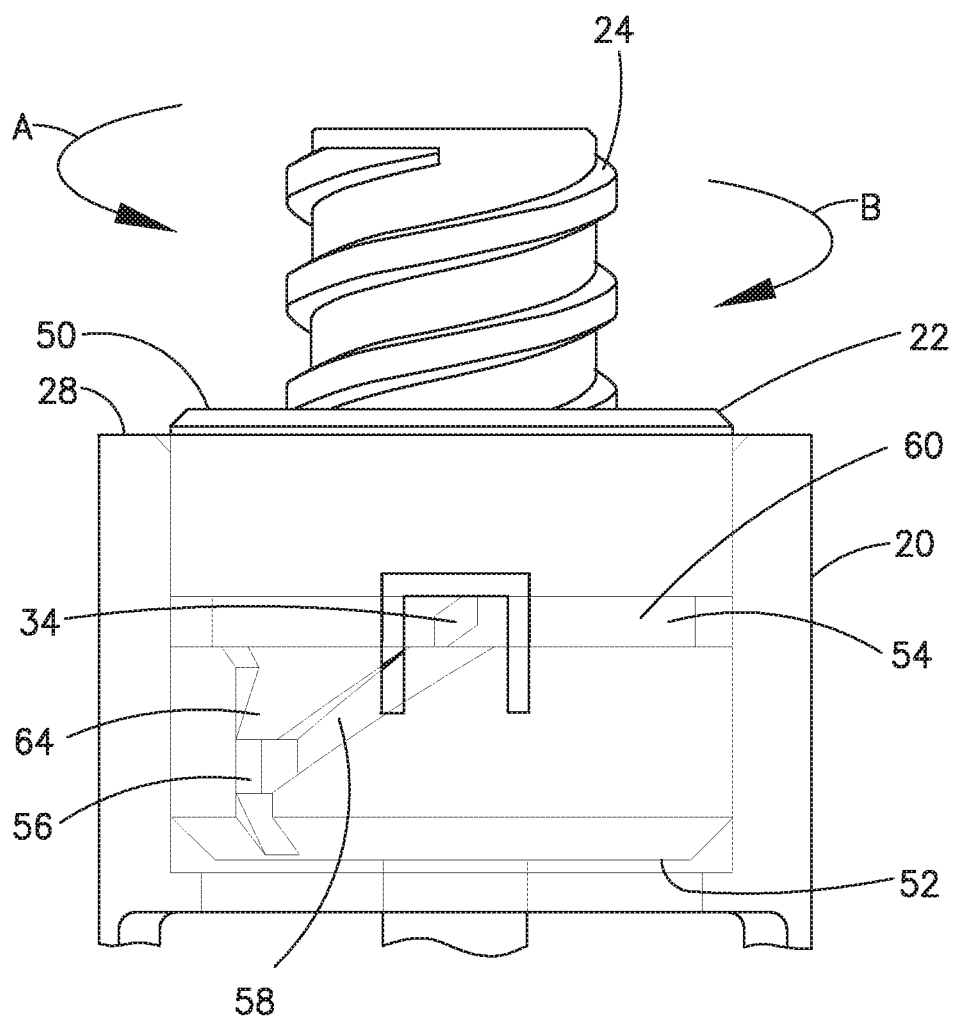
FIG. 10 is a partial front view of the syringe adapter of FIG. 1, showing a second position of a connector body with a housing shown transparent for clarity.

Referring to FIG. 10, the tab 34 of the housing 20 moves through the connecting portion 58 of the channel 54 with the torque required to rotate the connector body 22 relative to the housing 20 increasing due to the decreasing depth of the connecting portion 58 of the channel 54, as discussed above, until the tab 34 enters the connected portion 60 of the channel 54. The increasing torque required to rotate the connector body 22 also provides a tactile indication that the syringe is being tightened and reaching a fully secured position on the connector body 22. As discussed above, an audible indication is provided when the tab 34 enters the connected portion 60 of the channel 54 due to the tab 34 snapping into the connected portion 60 of the channel 54. The differences in the depth of the connecting portion 58 of the channel 54 and the connected portion 60 of the channel 54 prevents the tab 34 from re-entering the connecting portion 58 of the channel 54. Once the tab 34 is received within the connected portion 60 of the channel 54, the connector body 22 is in the second position and the first end 50 of the connector body 22 is coterminous with the first end 28 of the housing 20 to provide an indication that the connector body 22 is in the second position and that the syringe is fully secured to the connector body 22. When the connector body 22 is in the second position, the connector body 22 is freely rotatable in both the first and second rotatable directions A,B relative to the housing 20. Providing such free rotation when a syringe is connected to the connector body 22 inhibits the accidental disconnection of a syringe from the connector body 22 by requiring a specific movement to disconnect the syringe from the connector body 22, as discussed below. Further, allowing the syringe to rotate relative to the connector body 22 when connected to the connector body 22 also prevents any movement of the syringe from being transferred to a closed system transfer device component connected to the syringe adapter 10. Without such free rotation, movement of the syringe may cause corresponding movement of the syringe adapter 10 thereby causing torque to be applied to a patient line or other component, which can kink lines or possibly result in accidental disconnection of a component.

Figure 11:
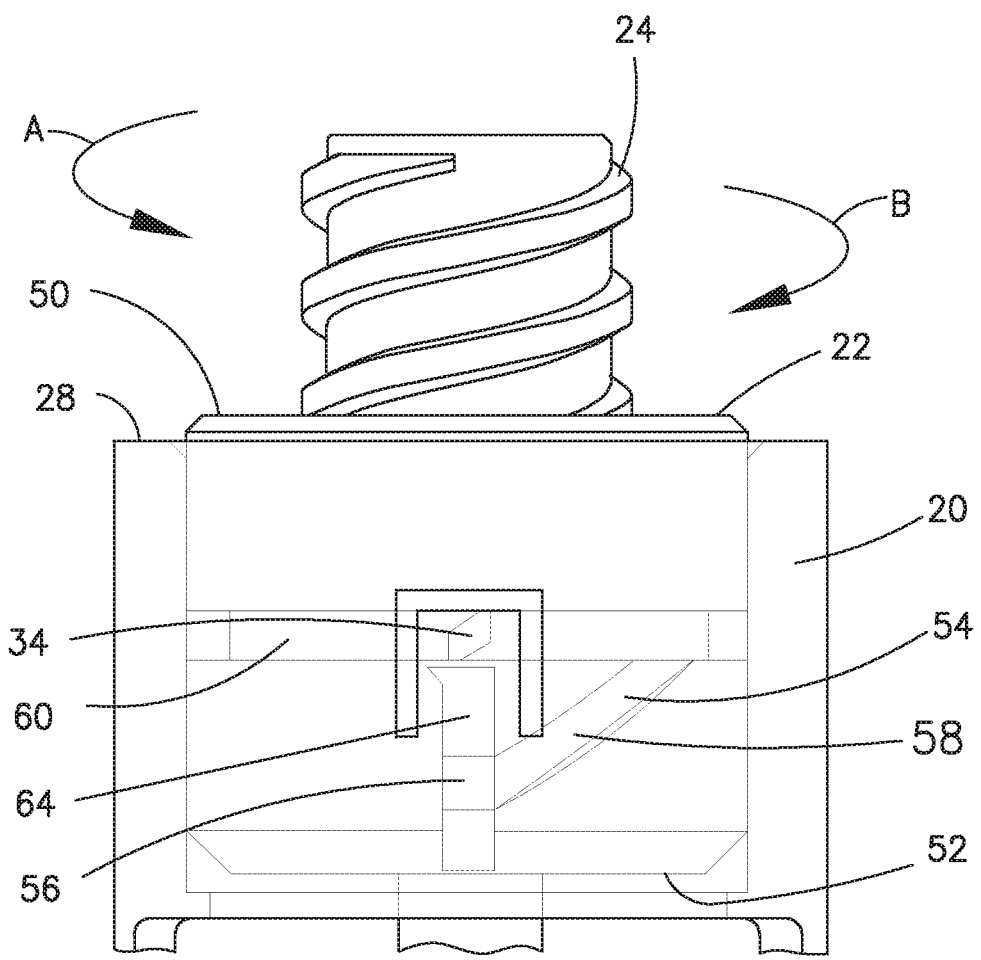
FIG. 11 is partial front view of the syringe adapter of FIG. 1, showing a second position of a connector body with a tab aligned with a reset portion of the channel and with the housing shown transparent for clarity.

Referring to FIG. 11, in order to disconnect a syringe from the connector body 22, the tab 34 of the housing 20 is aligned with the reset portion 64 of the channel 54. The tab 34 enters the reset portion 64 of the channel 54 by pulling the connector body 22 in an axial direction relative to the housing 20, which may be accomplished by pulling on the syringe connected to the connector body 22. Indicators may be provided on the connector body 22 and the housing 20 to provide an indication when the tab 34 is aligned with the reset portion 64 of the channel 54. Alternatively, a user can pull on the syringe while rotating the syringe which will cause the tab 34 to enter the reset portion 64 of the channel 54 when rotational movement of the connector body 22 aligns the tab 34 with the reset portion 64. The reset portion 64 of the channel 54 has the same or similar depth as the connected portion 60 of the channel 54 to allow the tab 34 to enter the reset portion 64. When the tab 34 enters the reset portion 64 of the channel 54, further axial movement of the connector body 22 away from the housing 20 causes the tab 34 to pass through the reset portion 64 and return to the start portion 56 of the channel 54. Due to the decreasing depth of the reset portion 64 of the channel 54, the tab 34 may snap into the start portion 56 of the channel 54 when entering the start portion 56 to provide an audible and/or tactile indication that the connector body 22 has returned to the first position. Once the tab 34 has entered the start portion 56 of the channel 54 with the connector body 22 in the first position, the syringe can be removed from the connector body 22 by rotating the syringe in the opposite direction used to secure the syringe onto the connector body 22. During disconnection of the syringe, the tab 34 of the housing 20 engages the stop face 62 to prevent rotation of the connection body 22 relative to the housing 20, which allows the removal of the syringe from the connector body 22 if require by healthcare professionals.

One or more tabs 34 and channels 54 may be utilized in connection with the syringe adapter 10. A small number of tabs 34, such as one or two, may require a larger force and torque to overcome, whereas many tabs 34 or a continuous tab 34 would require a smaller interferences per each tab 34. The channel 54 may snuggly fit the tab 34 when the tab 34 is in the connected portion 60 of the channel 54 to allow no axial movement of the connector body 22 relative to the housing 20. Alternatively, the connected portion 60 of the channel 54 may be wider than the tab 34 to allow axial movement between the housing 20 and the connector body 22, which would not allow forces applied axially to the connector body 22, unintentional or otherwise, to be translated to the connection between the syringe and the connector body 22.

Although the invention has been described in detail for the purpose of illustration based on what is currently considered to be the most practical and preferred aspects, it is to be understood that such detail is solely for that purpose and that the invention is not limited to the disclosed aspects, but, on the contrary, is intended to cover modifications and equivalent arrangements that are within the spirit and scope of the appended claims. For example, it is to be understood that the present invention contemplates that, to the extent possible, one or more features of any aspect can be combined with one or more features of any other aspect.

The invention claimed is:

1. A medical connector comprising:
a housing having a first end and a second end positioned opposite the first end, the housing defining a passageway; and
a connector body having a first end and a second end positioned opposite the first end, the connector body having a connection member configured to be secured to a mating connector, wherein one of the housing and the connector body includes a tab and the other of the housing and the connector body defines a channel that receives the tab, and wherein the connector body is movable relative to the housing between a first position where the connector body is restricted from rotating relative to the housing in a first rotational direction and free to rotate relative to the housing in a second rotational direction, and a second position where the connector body is free to rotate in the first and second rotational directions,
wherein the channel comprises a start portion, a connecting portion extending from the start portion, and a connected portion extending from the connecting portion, the connector body is in the first position when the tab is in the start portion of the channel, the connector body is in the second position when the tab is in the connected portion of the channel, and wherein the tab is in the connecting portion of the channel when the connector body transitions from the first position to the second position.

2. The medical connector of claim 1, further comprising a stop face adjacent to the start portion of the channel, the stop face configured to engage the tab to restrict movement of the housing in the first rotational direction.

3. The medical connector of claim 1, wherein the connected portion of the channel extends circumferentially around the connector body.

4. The medical connector of claim 1, wherein the connecting portion of the channel extends helically from the start portion of the channel to the connected portion of the channel, the connector body configured to axially move relative to the housing when the tab engages the connector body or the housing defining the connecting portion of the channel.

5. The medical connector of claim 4, wherein the first end of the connector body is spaced from the first end of the housing when the connector body is in the first position, and the first end of the connector body is coterminous with the first end of the housing when the connector body is in the second position.

6. The medical connector of claim 5, wherein the connection member of the connector body extends from the first end of the connector body.

7. The medical connector of claim 5, wherein the connector body comprises an indicator visible when the connector body is in the first position and non-visible when the connector body is in the second position.

8. The medical connector of claim 4, wherein a depth of the connecting portion of the channel decreases as the connecting portion extends from the start portion of the channel to the connected portion of the channel.

9. The medical connector of claim 1, wherein the channel further comprises a reset portion extending from the connected portion of the channel to the start portion of the channel, a depth of the reset portion of the channel decreasing from the connected portion of the channel to the start portion of the channel, wherein the tab is configured to move from the connected portion of the channel to the start portion of the channel via the reset portion of the channel.

10. The medical connector of claim 9, wherein the reset portion of the channel extends in an axial direction.

11. The medical connector of claim 1, wherein the tab is movable in a radial direction via a spring member.

12. The medical connector of claim 11, wherein the tab provides at least one of an audible and tactile indication when moved from the first position to the second position.

13. The medical connector of claim 12, wherein the audible indication or tactile indication comprises the tab engaging the connector body when the connector body is moved into the second position.

14. The medical connector of claim 11, wherein the spring member comprises a cantilever spring.

15. The medical connector of claim 1, wherein the connector body is received by the passageway of the housing, the tab extending radially inward from the housing into the channel of the connector body.

16. The medical connector of claim 1, wherein the connection member comprises a female luer connection.

17. A syringe adapter comprising:
a housing having a first end and a second end positioned opposite the first end, the housing defining a passageway; and a connector body having a first end and a second end positioned opposite the first end, the connector body having a connection member configured to be secured to a syringe barrel, wherein one of the housing and the connector body includes a tab and the other of the housing and the connector body includes a channel that receives the tab, the tab is movable in a radial direction via a spring member, wherein the connector body movable relative to the housing between a first position where the connector body is restricted from rotating relative to the housing in a first rotational direction and free to rotate relative to the housing in a second rotational direction, and a second position where the connector body is free to rotate in the first and second rotational directions, and wherein the channel comprises a start portion, a connecting portion extending from the start portion, a connected portion extending from the connecting portion, and a reset portion extending from the connected portion of the channel to the start portion of the channel, the connector body is in the first position when the tab is in the start portion of the channel, the connector body is in the second position when the tab is in the connected portion of the channel, the tab is in the connecting portion of the channel when the connector body transitions from the first position to the second position, and the tab is configured to move from the connected portion of the channel to the start portion of the channel via the reset portion of the channel.

18. The syringe adapter of claim 17, wherein the connecting portion of the channel extends helically from the start portion of the channel to the connected portion of the channel, the connector body configured to axially move relative to the housing when the tab engages the connector body or housing defining the connecting portion of the channel, wherein a depth of the reset portion of the channel decreases from the connected portion of the channel to the start portion of the channel, and wherein a depth of the connecting portion of the channel decreases as the connecting portion extends from the start portion of the channel to the connected portion of the channel.

19. The syringe adapter of claim 18, wherein the first end of the connector body is spaced from the first end of the housing when the connector body is in the first position, and the first end of the connector body is coterminous with the first end of the housing when the connector body is in the second position.

* * * * *

UNITED STATES PATENT AND TRADEMARK OFFICE
CERTIFICATE OF CORRECTION

PATENT NO. : 11,040,153 B2  
APPLICATION NO. : 16/381489  
DATED : June 22, 2021  
INVENTOR(S) : Jayeon Kim et al.

Page 1 of 1

It is certified that error appears in the above-identified patent and that said Letters Patent is hereby corrected as shown below:

In the Claims

Column 11, Line 10, Claim 17, after "body" insert -- is --

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*